United States Patent [19]
Shockey et al.

[11] Patent Number: 5,275,151
[45] Date of Patent: Jan. 4, 1994

[54] HANDLE FOR DEFLECTABLE CATHETER

[75] Inventors: Rick L. Shockey, Coon Rapids; Whitney A. McFarlin, Minneapolis; Steven M. Blakemore, Ramsey, all of Minn.

[73] Assignee: Clarus Medical Systems, Inc., Minneapolis, Minn.

[21] Appl. No.: 804,933

[22] Filed: Dec. 11, 1991

[51] Int. Cl.$^5$ ............................................. A61B 1/00
[52] U.S. Cl. ................................ 128/4; 604/95; 606/46; 128/772
[58] Field of Search ............... 128/772, 4, 6; 606/46, 606/13, 127, 194; 604/95; 138/118

[56] References Cited

U.S. PATENT DOCUMENTS

| | | | |
|---|---|---|---|
| 3,850,175 | 11/1974 | Iglesias | 606/46 |
| 4,421,106 | 12/1983 | Uehara | 128/4 |
| 4,492,230 | 1/1985 | Sunago et al. | 606/13 |
| 4,586,923 | 5/1986 | Gould et al. | 604/95 |
| 4,686,965 | 8/1987 | Bonnet et al. | 128/4 |
| 4,737,142 | 4/1988 | Heckele | 604/95 |
| 4,799,496 | 1/1989 | Hargreaves et al. | 128/772 |
| 4,898,577 | 2/1990 | Badger et al. | 606/194 X |
| 4,917,094 | 4/1990 | Lynch et al. | 128/772 |
| 4,996,974 | 3/1991 | Ciarlei . | |
| 5,098,412 | 3/1992 | Shiu | 128/772 X |
| 5,117,839 | 6/1992 | Dance | 128/772 |

OTHER PUBLICATIONS

Onik, G., et al., "Automated Percutaneous Discectomy: Preliminary Experience", *Acta Neurochirurgica, Suppl.* 43: 58-62 (1988).
Schreiber, Adam, et al., "Does Percutaneous Nucleotomy With Discoscopy Replace Conventional Discectomy? Eight Years of Experience and Results in Treatment of Herniated Lumbar Disc". *Clinical Orthopaedics and Related Research*, 238: 35-42 (Jan. 1989).
Onik, G., et al., "Automated Percutaneous Discectomy at the L5-S1 Level; Use of a Curved Cannula": *Clinical Orthopaedics and Related Research*, 238: 71-76 (Jan. 1989).
Yonezawa, Takumi, et al., "The System and Procedures of Percutaneous Intradiscal Laser Nucleotomy". *Spine.* 15(11): 1175-1185 (1990).

*Primary Examiner*—Richard J. Apley
*Assistant Examiner*—Karen A. Jalbert
*Attorney, Agent, or Firm*—Haugen & Nikolai

[57] ABSTRACT

A handle device for an endoscope incorporates controls for adjusting the degree of curvature of the distal tip portion of the endoscope as well as the degree of extension of the surgical instrument beyond the distal end of the endoscope's working lumen. The handle member comprises a generally hollow body which is dimensioned to be readily grasped by the surgeon and it incorporates a thumb-slide having a ratchet surface thereon, the thumb-slide being joined to a pull-wire extending the length of the endoscope and fastened at its distal end to the body of the endoscope. By depressing and longitudinally sliding the thumb-slide, the curvature of the distal end of the steerable endoscope is controlled. The degree of extension of the working instrument beyond the distal end of the working lumen is controlled by a rotatable threaded rod which is designed to produce only translational motion to the instrument without any twisting thereof. The handle member also includes provisions for introducing a flushing liquid into the endoscope's working lumen but without flooding the interior of the handle.

24 Claims, 3 Drawing Sheets

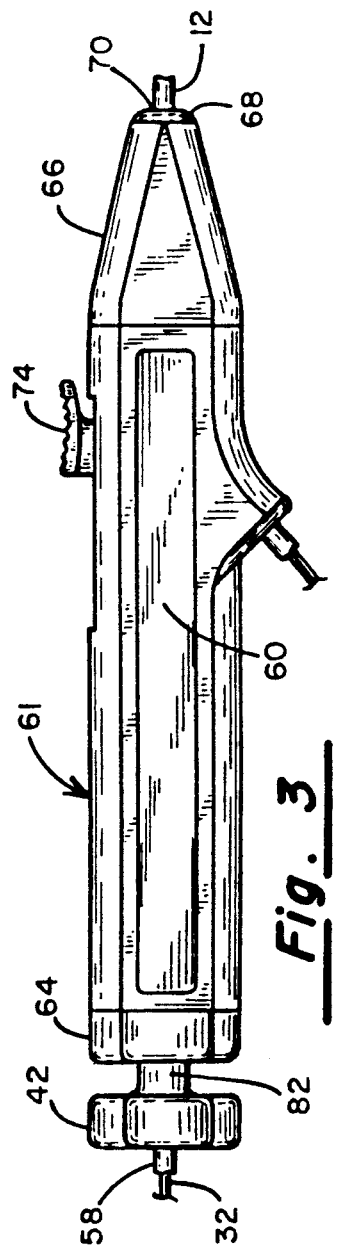
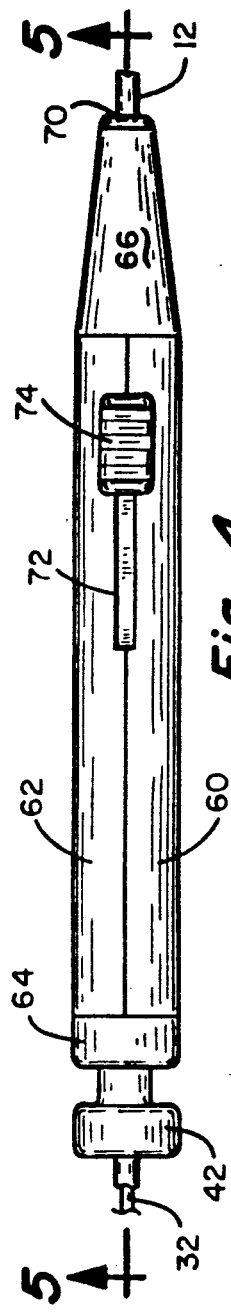
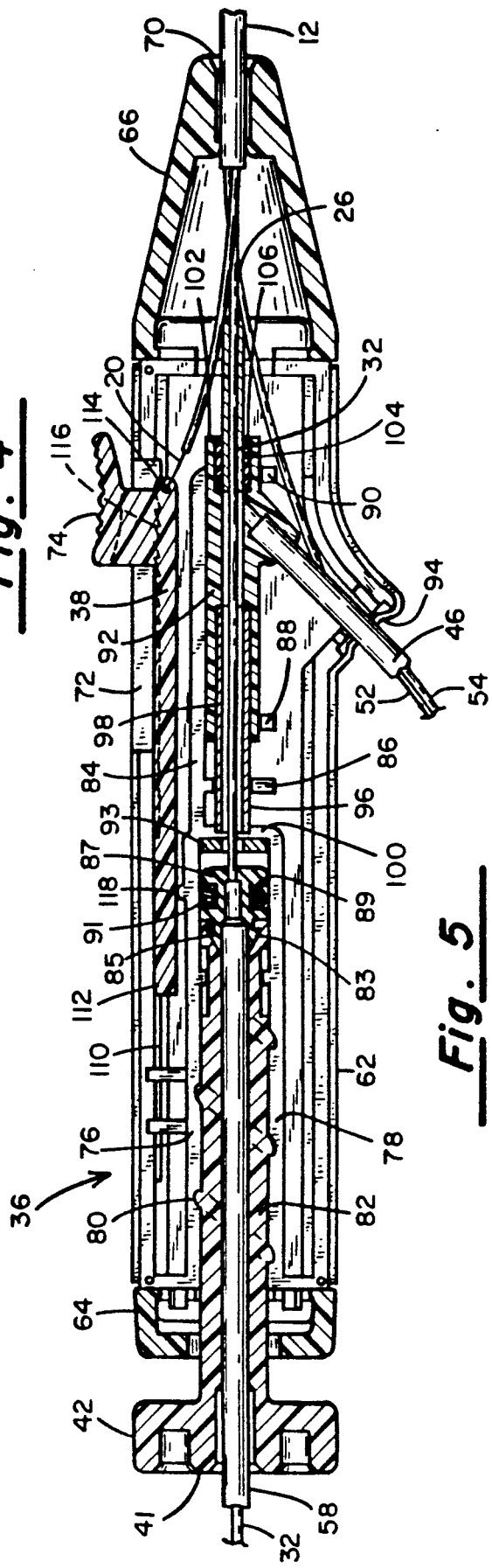

HANDLE FOR DEFLECTABLE CATHETER

BACKGROUND OF THE INVENTION

I. Field of the Invention

This invention relates generally to surgical apparatus, and more particularly to a handle for use with a deflectable endoscope which is human-engineered to permit the surgeon to control the deflection of the distal tip of the endoscope from the proximal end thereof and for manipulating a surgical instrument within the working lumen of the endoscope.

II. Discussion of the Prior Art

Over the past few years, significant advances have been made in the manner in which many surgical procedures are carried out. In so-called "minimally invasive surgery", often referred to by the acronym, MIS, rather than making large incisions to gain access to an internal organ or other tissue to be excised, small punctures are made allowing a viewing endoscope to be inserted and advanced to the organ or other tissue to be surgically addressed. The endoscope will typically include an elongated catheter having a plurality of lumens for accommodating optical fibers or fiber bundles so that light energy may be transmitted from a source at the proximal end of the endoscope to its distal tip for illuminating the surgical site. Other optical fibers may be used to transmit an image being illuminated back to the proximal end of the endoscope for viewing by the physician. Still another channel or lumen may be reserved for the surgical instrument itself, which is to be used to effect the cutting. Surgical instruments may typically include a laser fiber, when laser energy is to be used to cut or ablate the tissue, or may accommodate a variety of electrosurgical instruments, e.g., forceps, scalpel, or other devices for grasping and retracting tissue out through the working lumen.

Devices of the type described are now being used in a variety of laparascopic procedures, in percutaneous discectomies for resolving herniated disks in the spinal column, in arthroscopic surgery, etc.

A variety of endoscopes, also known in the art, include a steerable distal tip. Such an endoscope will commonly include a lumen containing a pull-wire whose distal end is anchored to the distal end portion of the endoscope and whose proximal end may be tensioned to thereby bend and deflect the distal end portion of the endoscope. By this means, the surgeon may gain purchase to areas to be surgically treated that cannot be reached head-on.

It is extremely desirable that the endoscope be provided with a handle at its proximal end where the handle includes the necessary controls for not only steering the distal tip of the endoscope, but also for controlling the longitudinal displacement of the surgical instrument contained within the working lumen of the endoscope. Generally speaking, prior art handles incorporating such controls have tended to be quite complex and expensive to manufacture making it cost-prohibitive to dispose of the endoscope after only a single use. As such, the prior art endoscopes had to be designed to permit them to be cleaned and sterilized between uses with different patients.

OBJECTS

It is accordingly a principal object of the present invention to provide an improved handle for use with an endoscope which is simple and inexpensive to manufacture.

Another object of the invention is to provide an improved handle for an endoscope which includes convenient controls for allowing the surgeon to steer the distal end of the endoscope and to control the movement of surgical instruments within the working lumen of the endoscope.

SUMMARY OF THE INVENTION

The foregoing objects and advantages of the invention are achieved in accordance herewith by providing a handle device for an endoscope where the endoscope is of the type having a tubular catheter with a steerable distal tip controlled by pull-wire extending the length of the catheter and with a working lumen for receiving a surgical instrument therein. The handle itself comprises a generally hollow body member whose length and width dimensions allow it to be readily and conveniently grasped in the palm of one hand. The body member is preferably fabricated from a medical grade plastic using a molding process where the handle itself is made in two, bilaterally symmetrical halves which are subsequently bonded together along their respective peripheral edges. The body member includes a longitudinal slot formed through the wall thereof to the hollow interior and the slot extends in the distal direction from an elongated guideway formed internally of the hollow handle. A thumb-slide, having ratchet teeth on a surface thereof, is fitted into the guideway with a thumb-engaging button projecting outwardly from the body member through the slot. This thumb-slide is connected to the proximal end of the pull-wire and by depressing the thumb-slide while moving it in the longitudinal direction, the distal tip of the endoscope is curved by varying degrees. Release of the thumb-slide allows the ratchet teeth to engage and hold a desired curvature setting.

When the two symmetrical halves of the body member are joined together, a cylindrical bore is created internally of the handle, the bore including a helical groove of a predetermined pitch. Fitted into this bore is a cylindrical rod having helical threads thereon of the same predetermined pitch such that they engage the helical groove in the bore. A portion of the cylindrical rod extends outward of the body member at its proximal end and includes a knob to facilitate its rotation. The surgical instrument disposed in the working lumen of the endoscope is coupled at its proximal end to the distal end of the cylindrical rod whereby rotation of the rod translates the surgical instrument within the working lumen.

The handle of the present invention also includes a provision for introducing a flushing fluid, such as saline, into the working lumen of the catheter to which the handle is affixed but without having the flushing fluid leaking out of the handle. This is accomplished by providing a tubular sealing means through which the surgical instrument may pass, but which is appropriately bonded to support structures within the generally hollow handle to preclude leakage of flushing fluid exterior to that seal.

DESCRIPTION OF THE DRAWINGS

The various constructional features and manner of assembly of the endoscope handle of the present invention will better be understood from the following detailed description of a preferred embodiment, especially when considered in conjunction with the accompanying drawings in which like numerals in the several views refer to corresponding parts.

FIG. 3 is a side elevation of the handle portion of the apparatus of FIG. 1;

FIG. 4 is a top elevation view of the handle portion of FIG. 3;

FIG. 5 is a cross-sectional view taken along the lines 4—4 in FIG. 3; and

DESCRIPTION OF THE PREFERRED EMBODIMENT

Figure 1:
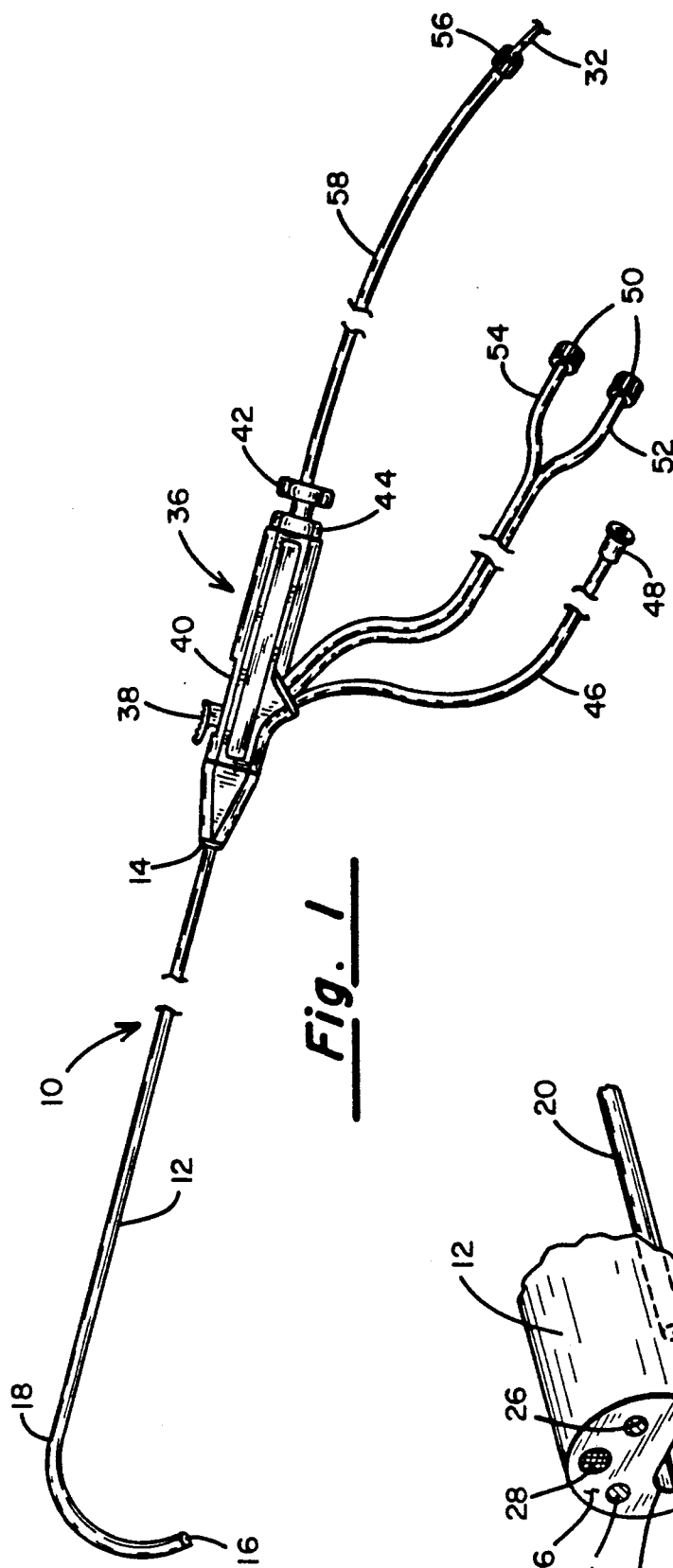
FIG. 1 is a perspective view of a typical endoscope incorporating the handle of the present invention.

Referring now to FIG. 1, there is indicated generally by numeral 10 an endoscope designed for carrying out a variety of MIS procedures. It is seen to include an elongated endoscope having a generally rigid shaft 12. The endoscope may be fabricated in accordance with the teachings of co-pending application of Rick L. Shockey, Ser. No. 765,989, filed Sep. 26, 1991, and entitled "DEFLECTABLE ENDOSCOPE", which is assigned to applicant's assignee. As such, it includes a tubular plastic outer sheath surrounding at least one rigid tube which may be formed from stainless steel hypodermic stock. The stainless steel tube extends along the length of the shaft 12 from its proximal end 14 toward but short of, its distal end 16. The stainless steel reinforcing tube may, for example, terminate at a location identified by numeral 18 in FIG. 1. In accordance with the invention of that aforereferenced application, a pull-wire 20 (FIG. 2) may pass through the stainless steel tube in the shaft 12 with its distal end 22 being anchored to the sheath 12 near its distal end 16.

Figure 2:
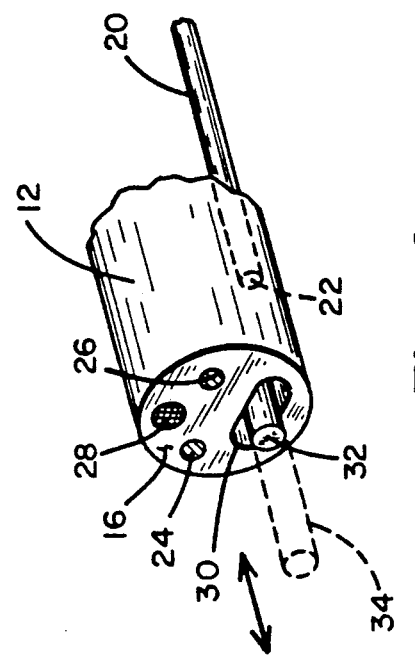
FIG. 2 is a greatly enlarged perspective view of the distal tip portion of the endoscope of FIG. 1.

With continued reference to FIG. 2, the tubular sheath 12 may also contain a plurality of lumens, including lumens 24 and 26, for accommodating optical fibers for illuminating the area around and surrounding the distal end 16 of the endoscope. The lumen 28 accommodates either a fiber-optic bundle for transmitting an optical image back to the proximal end of the endoscope assembly or, alternatively, a video camera chip and the necessary electrical conductors for powering the chip and for transmitting digital signals representative of the image back to viewing apparatus (not shown) coupled to the proximal end of the endoscope.

Numeral 30 identifies the working lumen of the endoscope and in the view of FIG. 2, it is seen to contain a laser fiber 32 through which laser energy may be transmitted to the site where the surgical cutting is to take place. As represented by the dotted line extension 34 of the laser fiber 32, means are provided for extending and retracting that laser fiber to allow it to be brought into contact with the body tissue to be cut.

Referring again to FIG. 1, joined to the proximal end 14 of the endoscope 10 is a handle indicated generally by numeral 36. It is this handle that comprises the present invention and its construction and operating features will be further explained hereinbelow. Suffice it now to say, the handle incorporates mechanisms whereby the physician can readily adjust the degree of bend of the distal tip portion of the endoscope as well as the length of extension of the optical fiber 32 beyond the distal end 16 of the endoscope body 12. In particular, the degree of bending of the distal portion of the endoscope is controlled by a thumb-slide 38 which projects through a longitudinal slot 40 formed in the handle body. The length of extension of the optical fiber 32 is adjusted and set by rotation of the knob 42 extending out from the proximal end 44 of the handle.

Before discussing the constructional features of that handle, it is felt beneficial to point out that a tube 46 may be joined by an appropriate fitting 48 to a source of flush liquid which is made to flow through the tube 46 and down the working lumen 30 of the endoscope sheath 12. Connector 50 is adapted to be coupled to a light source whereby light may be transmitted through optical fibers contained within the outer sheath 52 and then through the lumens 24 and 26 to the distal end 16 of the endoscope. The image information is transmitted back through lumen 28 and via cable 54 to an appropriate device for displaying the scene illuminated by the light source. The laser fiber 32 is adapted to be coupled to a laser generator by a coupler 56. It passes through a tubular jacket 58 into the handle 36, via a bore formed through the knob 42. The laser fiber 32 in jacket 58 is appropriately routed through the handle and thence down the working lumen 30 of the endoscope sheath 12.

Referring now to FIGS. 3 and 4, it can be seen that the handle member of the present invention comprises first and second generally bilaterally symmetrical halves 60 and 62 which are preferably formed in a molding operation from a suitable medical grade plastic, such as a polycarbonate or a polystyrene. The two halves are joined together along their peripheral edges. The two halves may be joined in any one of a number of bonding methods. Each of the handle halves includes an abutment surface 61 extending from the bottom portion thereof for engaging the surgeon's forefinger and acting as a stop to prevent slippage of the handle when it is being grasped in the palm of the hand. A proximal end cap 64 is designed to snap over the proximal ends of the halves 60 and 62. Likewise, a distal end cap 66 is fitted onto the distal end of the body halves 60 and 62. The distal end cap 66 tapers in both the vertical and horizontal direction to form a distal nose portion 68 having a central opening 70 formed therethrough for receiving the endoscope tube 12 therein.

As can best be seen in the top view of FIG. 4, a recess is formed in the upper peripheral edge of each of the side members 60 and 62 so as to create a longitudinal slot 72 along the top median line of the handle 61. Extending upward through the slot 72 is a thumb-receiving pad 74 of a thumb-slide member which will be described in greater detail when the internal constructional features of the handle 61 are explained.

Extending through an aperture formed centrally in the proximal end cap 64 is a cylindrical rod which terminates at its proximal end in a knob 42. As will be further explained, rotation of the knob 42 is effective to produce longitudinal displacement of the surgical instrument with which the handle member 61 is being used. For purposes of explanation, the surgical instrument is described as being a laser fiber, it being understood, however, that other instruments may be deployed in the working lumen and controlled by the handle of the present invention.

Referring now to FIG. 5 which is a longitudinal cross-sectional view taken along the line 5—5 in FIG. 4, interior structures of the handle become visible. Extending laterally outward from the interior surface of the handle half 62 is a semi-circular, integrally molded sleeve 76 which, together with the corresponding segment of the handle half 60 defines a cylindrical bore 78 with a helical groove of a predetermined pitch 80 formed inwardly thereof and extending along its length. Fitted into this bore 78 is the previously mentioned generally cylindrical rod, identified as 82, which has formed on its exterior surface a raised thread of the same predetermined pitch as that of the groove 80 formed in the cylindrical bore 78. A stem portion of the rod 82 extends outwardly beyond the proximal end of the proximal end cap 64 and formed on the terminus thereof is the knob 42 which may be grasped by the surgeon and used to facilitate rotation of the rod 82. As can further be seen in the cross-sectional view of FIG. 5, a longitudinal, concentrically disposed bore 41 extends through the knob 42 and the rod 82, allowing the laser fiber 32 to pass therethrough. The rod 82 terminates as its distal end in a dove-tail slot 83 into which is fitted a corresponding dove-tail 85 formed integrally with a cylindrical head 87. The laser fiber 32 passes through a longitudinal bore in the head 87 and is bonded within the bore by a suitable adhesive. In this fashion, rotation of the knob 42 results in only longitudinal motion (without rotation) of the head 87, preventing the twisting and ultimate breakage of the optical fiber. An annular groove 89 formed in the head member 87 accommodates an O-ring 91 which is dimensioned to form a resilient interference fit with the interior side wall of the segment 76 to create a mechanical drag, preventing the free spinning of the rod 82. Rotation in the counterclockwise direction causes the rod 82 to translate in the proximal direction while clockwise rotation of the knob 42 results in movement of the rod 82 in the distal direction.

In that the handle of the present invention may be used with a variety of endoscopes and surgical instruments used therewith, the amount of travel of the surgical instrument may be set at the time of production of the handle by inserting one or more annular spacers as at 93 within the tubular sleeve 76 and distal of the head member 87.

Integrally formed with the sleeve segment 76 and extending in the distal direction therefrom is a rib member 84 which projects inwardly from the interior wall of the handle half 62 so as to abut a similar rib which projects inwardly from the handle half 60. Extending down from the rib 84 and at longitudinally spaced locations are a series of C-shaped support members 86, 88 and 90 which are generally semi-circular in shape and have a central semi-circular opening formed through the thickness dimension thereof. When the support members 86 and 88 mate with the corresponding support members formed in the handle half 60, a series of circular openings are formed.

Fitted into the circular openings defined by the support members 88 and 90 and the corresponding support members of the handle half 60 (not shown) is a Y-tube member 92 which allows a flushing liquid to be introduced, via a length of plastic tube 46, which is in fluid communication with the working lumen of the endoscope. In that the laser fiber 32 must also pass through the working lumen, a means must be provided for reliably sealing the assembly so that the flushing liquid is precluded from flowing through the voids in the handle member 36. This is achieved by providing a sealing tube 96 which fits tightly within a counterbore 98 formed in the a first leg of Y-tube 92, the sealing tube being also sealed to the molded support member 100 located at the distal end of the molded sleeve member 76.

The Y-tube 92 has a cylindrical bore 102 formed in the distal end thereof and fitted into that bore is a tubular jacket 104 which loosely surrounds the laser fiber 32. The tubular jacket 104 is preferably fabricated from stainless steel hypodermic stock and it passes into the working lumen 30 of the endoscope 12. A plastic annular gasket 106 is inserted into the bore 102 in the Y-tube and insures a liquid-tight seal between the exterior of the tubular jacket 104 and the I.D. of the bore 102 formed in the Y-tube. Using this approach, a flushing liquid, such as saline, introduced through the flush tube 46 feeds into the working lumen 30 of the endoscope 12 via the Y-tube 92 and the jacket 104 surrounding the laser fiber 32.

As already mentioned, the endoscope handle of the present invention incorporates a mechanism whereby the surgeon may readily bend and thereby steer the distal end portion of the endoscope. Referring still to FIG. 5, each of the handle halves 60 and 62 includes a guide groove 110 which together form a longitudinal guideway for receiving the thumb slide 38. The thumb slide itself has a generally planar strip 112 designed to slide within the guideway 110.

Projecting upwardly therefrom near its distal end is the thumb pad member 74. The thumb pad member 74 extends exteriorly of the handle through the slot 72. Passing through the distal end portion of the strip 112 is a small aperture 114 through which a hook formed on the end of the pull wire 20 passes. The upper surface of the thumb slide 38 is provided with a detent in the form of ratchet teeth, as at 116, which are arranged to mate with corresponding ratchet teeth formed on the undersurface of the handle halves 60 and 62 along side the slot 72. In that the slide member 38 is molded from plastic and has a somewhat elongated strip 112 passing over a fulcrum 118 protruding from the exterior of the sleeve 76, depression of the thumb pad 74 will cause the ratchet teeth 116 to disengage from the mating teeth on the handle halves, allowing the thumb slide 38 to be moved either proximally or distally within the guide slot 72. Release of the downward pressure on the thumb pad 74 will allow the teeth to re-engage, thereby holding the setting established for the pull wire 20 and, thus, the curvature of the distal tip of the endoscope.

In addition to the flush tube 46 which enters the interior of the handle to join with the Y-tube 92 via grommet 94 in the abutment surface 61 are the optical fibers 52 and 54 used to transmit the illumination to the distal end of the endoscope and to convey the image observed back to the display equipment (not shown) mentioned earlier.

ALTERNATIVE EMBODIMENT

Figure 6:
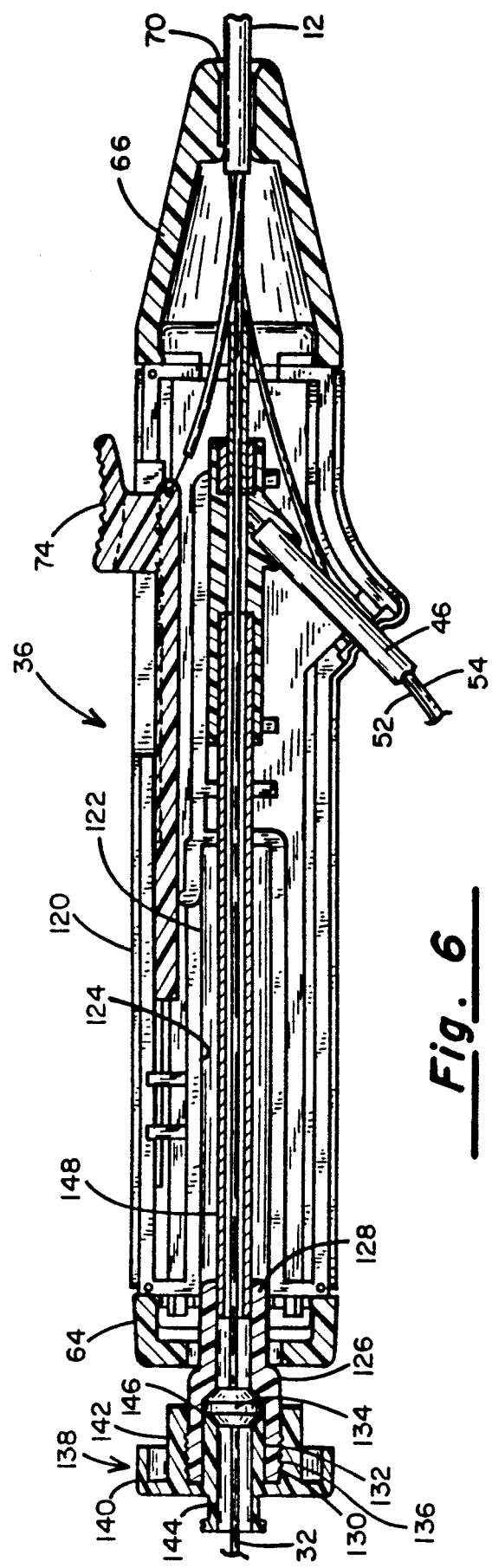
FIG. 6 is a longitudinal cross-sectional view of an alternative embodiment of a handle for an endoscope.

In the alternative arrangement illustrated in the cross-sectional view of FIG. 6, the handle member again comprises first and second generally bilaterally symmetrical halves as at 120 formed in a molding operation. The two halves join together along their peripheral edges. The housing half 120 differs from that of housing half 62 in FIGS. 4 and 5 in that instead of providing semicircular integrally molded segments like segment 76 in FIG. 5 that has a helical groove of a predetermined pitch formed along its length, the semicircular segment 122 in FIG. 6 is smooth and defines a cylindrical bore 124. Fitted through the end cap 64 and into the bore 124 is a first element 126 of a Touy Borst clamp. The element 126 includes a tubular distal portion 128 fitted through the end cap 64 and into the bore 124. The integrally formed proximal segment 130 of element 126 includes a counterbore 132 forming a chamber for an elastomeric valve member 134. The proximal end portion of the member 130 includes a threaded surface 136 which is intended to mate with a molded plastic end cap 138.

The elastomeric valve member 134 is generally hollow and includes a circular opening formed on the proximal facing and distal facing end surfaces thereof. It fits within a close tolerance of the counterbore 132 and allows the laser fiber 32 or other laparascopic instrument to pass through it.

The cap member 138 includes an annular finger grip portion 140 which surrounds an internally threaded sleeve 142. The internally threaded sleeve 142 is arranged to cooperate with the threads 136 on member 126. As is illustrated in the exploded view of FIG. 6, the rotatable cap 138 is designed to fit over the optical fiber 32 which passes through a central bore 144 of the end cap. When the end cap 138 is only loosely threaded onto the end of member 126, the distal end 146 abuts but does not compress the elastomeric member 134. When, however, the end cap 138 is screwed down onto the stem 130, the distal end 146 engages and compresses the elastomeric member 134, causing it to tightly grip the exterior surface of the laser fiber 32 and preventing movement thereof.

The laser fiber 32 or whatever other instrument may be used with the device of the present invention passes through a tube 148 fitted into the distal portion 128 and, as such, provides longitudinal support for the working element.

The alternative embodiment of FIG. 6 allows the surgeon to clamp and unclamp the optical fiber 32 and when unclamped to advance the optical fiber either in the distal direction or the proximal direction as the case may be. In all other respects, the embodiment of FIG. 6 may be identical to that of the earlier described embodiment and those features need not be repeated here.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A handle device for an endoscope, the endoscope being of the type having a tubular catheter having a proximal end and distal end with a steerable distal tip controllable by a pull-wire extending the length of said catheter and a working lumen for receiving a surgical instrument therein, the handle device comprising:
   (a) a generally hollow body member with length and width dimensions permitting it to be readily grasped in the palm of one hand and including a proximal end and a distal end, said body member including a longitudinal slot formed therethrough to the hollow interior thereof, said slot extending in the distal direction from an elongated guideway formed internally of said hollow body member, said hollow body member further including a cylindrical bore extending inward from said proximal end, the bore including a helical groove of a predetermined pitch;
   (b) means disposed at said distal end of said body member for attachment to said proximal end of said tubular catheter;
   (c) slide means fitted into said guideway and including a finger-engaging portion projecting outwardly of said body member through said slot, said slide means being connected to said pull-wire for controlling the disposition of said distal tip of said catheter as said slide means is moved in said guideway and slot;
   (d) a cylindrical rod fitted into said bore and having helical threads thereon of said predetermined pitch for engaging said helical groove in said bore, at least a portion of said rod extending outward of said body member at its proximal end, said portion being graspable by the surgeon's fingers for rotation; and
   (e) means for joining said cylindrical rod to the surgical instrument disposed in the working lumen of said endoscope whereby rotation of said rod translates the surgical instrument within said working lumen.

2. The handle device as in claim 1 and further including detent means on said slide means and said body member adjacent said longitudinal slot for selectively latching said slide means at desired locations along said guideway.

3. The handle device as in claim 2 wherein said detent means comprises ratchet teeth on said slide means engageable with ratchet teeth on said body member adjacent said slot.

4. The handle device as in claim 3 wherein said slide means is depressible within said slot in a direction transverse to said slot for selectively disengaging said ratchet teeth.

5. The handle device as in claim 1 wherein said means for joining said cylindrical rod to said surgical instrument includes a coupling which is non-rotatable relative to said body member when said cylindrical rod is rotated whereby only longitudinal translational motion is imparted to said surgical instrument when said cylindrical rod is rotated.

6. The handle device as in claim 5 wherein said cylindrical rod includes a concentric bore extending the full length thereof for receiving a surgical instrument therethrough, said concentric bore being in general alignment with said working lumen of said catheter.

7. The handle device as in claim 6 and further including:
   (a) means in said body member for introducing a flushing liquid into said working lumen of said catheter; and
   (b) sealing means for preventing said flushing liquid from filling the hollow interior of said body member.

8. The handle device as in claim 7 wherein said body member includes a plurality of annular support members formed interiorly thereof in parallel, longitudinally-spaced relation and said flushing liquid introducing means comprises a Y-tube supported by said support members.

9. The handle device as in claim 8 having a sealing means comprising a deformable plastic tube with first and second ends coaxially disposed with said concentric bore in said cylindrical rod and supported along its length by said annular support members and joined at said first end to one end of said Y-tube, said second end of said plastic tube being sealingly affixed to one of said plurality of annular support members.

10. The handle device as in claim 1 wherein said body member comprises:
   (a) first and second bilaterally symmetrical body halves joined together along a common plane; and
   (b) a proximal end cap secured to said proximal end of said body member when said first and second body halves are joined.

11. The handle device as in claim 1 wherein said means disposed at said distal end of said body member comprises
   a distal end cap secured to said distal end of said body member.

12. The handle device as in claim 1 and further including insert means adapted to be disposed in said bore for determining the length of axial travel of said cylindrical rod upon its rotation.

13. A handle device for an endoscope, the endoscope being of the type having a tubular catheter with a working lumen for receiving a working instrument therein, the handle device comprising:
   (a) a pair of bilaterally symmetrical handle halves joined together to form a generally hollow body member whose length and width dimensions permit it to be conveniently grasped in the palm of one hand, said body member having proximal and distal ends, said body halves, when joined further defining an internal cylindrical bore having a helical groove of a predetermined pitch formed therealong;
   (b) a cylindrical rod fitted into said bore and having helical threads thereon of said predetermined pitch for engaging said helical groove in said bore with at least a portion of said cylindrical rod extending outward of said body member at its proximal end and being graspable by the surgeon for rotation; and
   (c) means for joining said cylindrical rod to a laser fiber whereby rotation of said rod translates said laser fiber allowing the distal end thereof to be selectively retracted and extended relative to the distal end of said endoscope.

14. The handle device as in claim 13 wherein said endoscope includes a steerable tip controllable by a pull-wire extending the length of said catheter and the handle device further including:
   (a) a longitudinal slot formed through said body member; and
   (b) slide means cooperating with said slot and with said pull-wire whereby longitudinal translation of said slide member in said slot bends the distal end portion of said endoscope.

15. The handle device as in claim 14 and further including ratchet teeth on said slide means and along the length of said slot for maintaining said slide means at predetermined locations along the length of said slot.

16. The handle device as in claim 13 and further including a concentric bore formed through the length of said cylindrical rod for receiving said laser fiber therein.

17. The handle device as in claim 16 wherein said cylindrical rod includes means for translating said laser fiber upon rotation of said cylindrical rod without rotating said laser fiber.

18. The handle device as in claim 13 and further including means for introducing a flushing fluid into said working lumen of said tubular catheter.

19. The handle device as in claim 18 wherein said means for introducing includes means for preventing leakage of said flushing liquid into the interior of said generally hollow body member.

20. A handle device for an endoscope, the endoscope being of the type including a tubular catheter having a working lumen for receiving a surgical instrument therein, the handle device comprising:
   (a) a generally hollow body member with length and width dimensions permitting it to be readily grasped in the palm of one hand and including a proximal end and a distal end in axial alignment with each other, said hollow body member further including a cylindrical bore extending inward from said proximal end;
   (b) means disposed at said distal end of said body member for attachment to said proximal end of said tubular catheter;
   (c) selectively releasable clamping means affixed to said proximal end of said hollow body member adapted for selectively preventing longitudinal displacement of said surgical instrument within said working lumen; and
   (d) means for introducing a flushing liquid through said hollow body member into said working lumen.

21. A handle device for an endoscope as in claim 20 wherein said tubular catheter has a steerable tip controlled by a pull-wire and said hollow body member includes a finger operated slide member coupled to said pull-wire.

22. The handle device as in claim 21 wherein said body member includes a longitudinal guideway for receiving said slide member.

23. The handle device as in claim 22 wherein said guideway is provided with a pattern of serrated teeth cooperating with serrated teeth on said slide member.

24. The handle device as in claim 20 wherein said clamping means comprises:
   (a) a tubular plug fitted into said proximal end of said body member, the plug including a longitudinal bore therein through which said surgical instrument can extend;
   (b) deformable elastomeric ring disposed in said longitudinal bore of said plug and surrounding a portion of said surgical instrument such that said surgical instrument can be displaced longitudinally when said ring is not deformed; and
   (c) means coupled to said tubular plug for selectively deforming said elastomeric ring and thereby clamp said surgical instrument against longitudinal movement.

* * * * *